United States Patent [19]

Pawloski

[11] 4,115,557

[45] Sep. 19, 1978

[54] SUBSTITUTED PYRIDINYL O-ALKYL PHENYL/PHOSPHONOTHIOATES AND THEIR USE AS PESTICIDES

[75] Inventor: Chester E. Pawloski, Bay City, Mich.

[73] Assignee: The Dow Chemical Company, Midland, Mich.

[21] Appl. No.: 788,400

[22] Filed: Apr. 18, 1977

Related U.S. Application Data

[63] Continuation-in-part of Ser. No. 649,433, Jan. 15, 1976, abandoned, which is a continuation-in-part of Ser. No. 568,220, Apr. 15, 1975, abandoned, which is a continuation-in-part of Ser. No. 456,943, Apr. 1, 1974, abandoned.

[51] Int. Cl.² .................. A01N 9/22; C07D 213/02
[52] U.S. Cl. .................. 424/200; 260/294.8 K; 71/94
[58] Field of Search ............ 260/294.8 K; 424/200

[56] References Cited

U.S. PATENT DOCUMENTS

| 3,478,037 | 11/1969 | Fest et al. | 260/294.8 K |
| 3,818,019 | 6/1974 | Rigterink | 260/294.8 K |

Primary Examiner—Alan L. Rotman
Attorney, Agent, or Firm—S. Preston Jones; C. Kenneth Bjork

[57] ABSTRACT

Substituted (2-)pyridinyl phosphonothioates are disclosed which are useful in the control of cotton leafworm larvae. The compounds are prepared by the reaction of selected substituted pyridinol and phosphonochloridothioate reactants.

68 Claims, No Drawings

SUBSTITUTED PYRIDINYL O-ALKYL PHENYL/PHOSPHONOTHIOATES AND THEIR USE AS PESTICIDES

CROSS-REFERENCE TO RELATED APPLICATION

This application is a continuation-in-part of application Ser. No. 649,433, filed Jan. 15, 1976, now abandoned, which in turn is a continuation-in-part of application Ser. No. 568,220, filed Apr. 15, 1975, now abandoned, which in turn is a continuation-in-part of application Ser. No. 456,943, filed Apr. 1, 1974, now abandoned.

PRIOR ART

Various substituted pyridinyl phenylphosphonothioates are known in the prior art and such known compounds include 0-(3,5,6-trichloro-2-pyridinyl) 0-methyl phenylphosphonothioate as taught in British Pat. No. 1,165,293, 0-(6-methyl-3-pyridinyl) 0-methyl phenylphosphonothioate as taught in Canadian Pat. No. 875,566 and British Pat. No. 1,250,911 and 0-(2-chloro-6-methyl-3-pyridinyl) 0-methyl phenylphosphonothioate as taught in German Pat. No. 2,132,590.

SUMMARY OF THE INVENTION

This invention relates to certain novel substituted-2-pyridinyl phenylphosphonothioates, hereinafter referred to for convenience as "active ingredients". The invention further concerns pesticidal compositions containing the aforesaid active ingredients as well as processes for controlling cotton leafworm larvae (*Spodoptera littoralis* Boisd.) with said active ingredients.

The novel substituted-2-pyridinyl phenylphosphonothioates of the present invention are those of the following general formula:

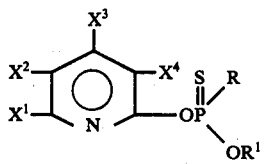

wherein R is phenyl or substituted phenyl; $R^1$ represents alkyl of 1 to 4 carbon atoms; and $X^1$, $X^2$, $X^3$ and $X^4$ each independently represent bromo, chloro, fluoro, trifluoromethyl or hydrogen, with the proviso that at least one of $X^1$, $X^2$, $X^3$ and $X^4$ is hydrogen; at least one of the others of $X^1$, $X^2$, $X^3$ and $X^4$ is other than hydrogen; with the added proviso that when $X^1$, $X^2$, $X^3$ or $X^4$ is selected from bromo, chloro or fluoro, that no more than two of $X^1$, $X^2$, $X^3$ and $X^4$ can be the same.

DETAILED DESCRIPTION OF THE INVENTION

The term "alkyl" as used herein and in the appended claims is employed to designate a straight- or branched-chain radical containing from one to four carbon atoms, such as, for example, methyl, ethyl, propyl, isopropyl, butyl, isobutyl and tert.-butyl. The term "substituted phenyl" is employed to designate a phenyl radical being mono- or polysubstituted with halogen, such as bromo, chloro or fluoro, or methyl radicals.

The active ingredients of the present invention are usually oily liquids at ambient temperatures, although some are obtained in solid form, and are soluble in usual organic carriers, such as, for example, carbon tetrachloride, acetone, toluene, methylene chloride, dimethylformamide and the like. The active ingredients of the above formula wherein R is phenyl, and $R^1$ is methyl or ethyl constitute a preferred embodiment of the present invention. In a further embodiment of the invention, compounds of the above formula wherein $X^1$ is bromo, chloro, fluoro or trifluoromethyl and $X^2$ and $X^4$ are hydrogen are a preferred class of compounds. Another preferred class of compounds are those wherein $X^1$ and $X^4$ are hydrogen and $X^2$ is bromo, chloro, fluoro or trifluoromethyl. An additional preferred class of compounds are those wherein $X^1$ and $X^2$ are hydrogen, $X^4$ is bromo, chloro, fluoro or trifluoromethyl. A further preferred class of compounds are those wherein $X^1$ is hydrogen or trifluoromethyl and $X^2$ and $X^4$ are independently bromo, chloro or fluoro. Another preferred class of compounds are those wherein $X^2$ is hydrogen and $X^1$ and $X^4$ are independently bromo, chloro or fluoro. An additional preferred class of compounds are those wherein $X^4$ is hydrogen and $X^1$ and $X^2$ are independently bromo, chloro or fluoro. Another preferred class of compounds are those wherein $X^1$ and $X^3$ are independently bromo, chloro or fluoro.

An especially preferred group of compounds of the present invention include those selected from the group consisting of 0-(6-chloro-2-pyridinyl) 0-methyl phenylphosphonothioate; 0-(6-fluoro-2-pyridinyl) 0-ethyl phenylphosphonothioate; 0-(6-chloro-2-pyridinyl) 0-ethyl phenylphosphonothioate and 0-(6-fluoro-2-pyridinyl) 0-methyl phenylphosphonothioate. Another particularly preferred group of compounds include those selected from the group consisting of 0-(5-chloro-2-pyridinyl) 0-ethyl phenylphosphonothioate; 0-(5-bromo-2-pyridinyl) 0-methyl phenylphosphonothioate, 0-(5-chloro-2-pyridinyl) 0-methyl phenylphosphonothioate and 0-(4-chloro-2-pyridinyl) 0-ethyl phenylphosphonothioate.

Another highly preferred group of compounds include those selected from the group consisting of 0-(3,5-dichloro-2-pyridinyl) 0-methyl phenylphosphonothioate; 0-(3,5-dibromo-2-pyridinyl) 0-methyl phenylphosphonothioate; 0-(3,5-dichloro-2-pyridinyl) 0-ethyl phenylphosphonothioate; 0-(3,5-difluoro-2-pyridinyl) 0-ethyl phenylphosphonothioate; 0-(4,6-dichloro-2-pyridinyl) 0-methyl phenylphosphonothioate; 0-(4,6-dichloro-2-pyridinyl) 0-ethyl phenylphosphonothioate; 0-(3,5-dichloro-6-fluoro-2-pyridinyl) 0-methyl phenylphosphonothioate; 0-(3,5-dichloro-6-(trifluoromethyl)-2-pyridinyl) 0-ethyl phenylphosphonothioate; 0-(6-bromo-3,5-dichloro-2-pyridinyl) 0-methyl phenylphosphonothioate; and 0-(5-bromo-3,6-dichloro-2-pyridinyl) 0-methyl phenylphosphonothioate.

The active ingredients of the present invention are prepared by reacting a substituted phosphonochloridothioate with a selected substituted 2-pyridinol or an alkaline salt thereof in the presence of an inert organic carrier. The reaction can be schematically illustrated as follows:

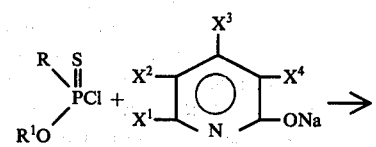

-continued

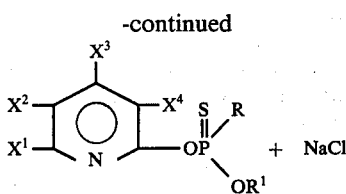
+ NaCl wherein all substituents are as previously defined.

The reaction is preferably carried out in the presence of an inert carrier medium such as, for example, benzene, toluene, xylene, acetone, methylisopropyl ketone, methylisobutyl ketone, acetonitrile, dimethylformamide, methylene chloride and the like. The reaction is further preferably carried out in the presence of an acid acceptor. For this purpose, the customary acid-binding agents can be employed. Those that are particularly suitable include, for example, alkali metal alcohololates and carbonates; such as potassium and sodium methylate or ethylate, sodium and potassium carbonate and tertiary amines such as, for example, triethylamine, trimethylamine, pyridine and the like. A small amount of a catalyst, such as mercuric chloride, trimethylbenzylammonium chloride, and the like is also preferably employed.

Ordinarily, a solution or suspension of a salt of the substituted 2-pyridinol reactant is first prepared and this is subsequently reacted with an appropriate phosphonochloridothioate. The reactants, as well as the auxiliary substances (acid-acceptors), are, in general, employed in stoichiometric amounts. The reaction temperature can be varied over in fairly wide range and, in general, the reaction is carried out at temperatures of from about 0° to about 100° C. (or the boiling point of the reaction mixture). Generally, the reaction is carried out, with agitation, for a period of from about one to about eight hours. The crude product is usually obtained in the form of viscous oils which can be freed from volatile impurities by heating at moderately elevated temperatures under reduced pressure. The refractive index can be used as a more precise determination of the product characterization.

The following non-limitative examples further illustrate the invention.

EXAMPLE I 0-(6-Chloro-2-pyridinyl) 0-methyl phenylphosphonothioate

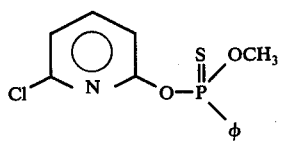

13 Grams (0.1 mole) of 6-chloro-2-pyridinol were suspended in 300 milliliters of methylisobutyl ketone and 8 grams of a 50 percent sodium hydroxide solution added thereto. The resulting mixture was heated under reflux conditions until the water of reaction was distilled out. The mixture was cooled in an ice water bath to about 4° C. and 20.6 grams (0.1 mole) of 0-methyl phenylphosphonothioic chloride added thereto. The resulting mixture was stirred for about one hour, then heated to a temperature of from about 40° to about 50° C. and maintained at such temperatures, with stirring, for a period of about one hour. Following this period, the reaction mixture was cooled by stirring at ambient temperatures for an additional period of about four hours and then mixed with 200 milliliters of ice water. After stirring the resulting aqueous mixture for a period of about ten minutes, the oily layer was separated and washed with two 150 milliliters portions of water. The oily product layer was then dried over calcium sulfate, filtered and distilled under reduced pressure until substantially all of the remaining solvent was removed. As a result of such operations, the desired 0-(6-chloro-2-pyridinyl) 0-methyl phenylphosphonothioate product was obtained as an amber oil having a refractive index ($n25/D$) = 1.5930. The nuclear magnetic reasonance (NMR) and infrared spectra (I.R.) confirmed the structure of the product.

EXAMPLE II 0-(6-Fluoro-2-pyridinyl) 0-methyl phenylphosphonothioate

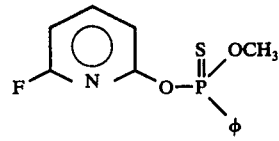

11.3 Grams (0.1 mole) of 6-fluoro-2-pyridinol, 14.0 grams (0.1 mole) of powdered potassium carbonate, 0.1 grams of mercuric chloride and 21.0 grams (0.1 mole) of 0-methyl phenylphosphonothioic chloride were mixed with 200 milliliters of acetonitrile and the resulting reaction mixture heated, with stirring, at temperatures of about 55° C. for a period of about five hours. The reaction mixture was cooled, filtered and distilled under reduced pressure until the solvent ceased to distill out (about 40° C.). The oily residue thus obtained was mixed with 300 milliliters of methylene chloride and the resulting mixture stirred with 300 milliliters of a 2 percent sodium hydroxide solution for about 15 minutes. The organic layer containing the desired product was separated, washed with water, again separated and dried over sodium sulfate. The oily product layer was filtered and distilled under reduced pressure at about 40° C. until substantially all of the solvent had been removed. As a result of such operations, the desired 0-(6-fluoro-2-pyridinyl) 0-methyl phenylphosphonothioate was obtained as an oil having a refractive index of $n(25/D)$ of 1.5791.

EXAMPLE III 0-(3,5-Dichloro-2-pyridinyl) 0-methyl phenylphosphonothioate

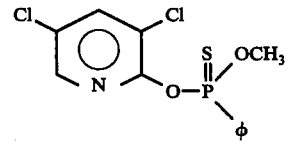

A mixture of 16.5 grams (0.1 mole) of 3,5-dichloro-2-pyridinol, 14.0 grams (0.1 mole) of potassium carbonate, 250 milliliters of acetonitrile, 0.1 gram of mercuric chloride and 21.0 grams (0.1 mole) of 0-methyl phenylphosphonochloridothioate was stirred at 50° C for four (4) hours. The reaction mixture was allowed to cool, filtered and the filtrate distilled under reduced pressure at 50° C until the solvent was removed. The oil which remained was taken up in 250 milliliters of methylene chloride and the resulting mixture stirred with 250 milliliters of a 2 percent sodium hydroxide solution. The organic layer was separated and washed twice with 200 milliliter portions of water, again separated and dried over sodium sulfate. The oily product was filtered and distilled under reduced pressure until substantially all of the solvent had been removed. The 0-(3,5-dichloro-2-pyridinyl) 0-methyl phenylphosphonothioate product was obtained as an oil in a yield of 23 grams (70 percent of theoretical) and had a refractive index of n(25/D) of 1.6093. The NMR spectra and I.R. spectra confirmed the structure of the product.

Example IV 0-(3,5-Dichloro-2-pyridinyl) 0-ethyl phenylphosphonothioate

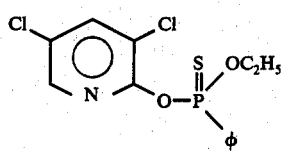

A mixture of 18.0 grams (0.11 mole) of 3,5-dichloro-2-pyridinol, 16.0 grams (0.11 mole) of potassium carbonate, 300 milliliters of methylene chloride and 0.2 gram of mercuric chloride was stirred at reflux for four hours. The reaction mixture was thereafter allowed to cool. To this mixture was added dropwise, a solution of 22.0 grams of 0-ethyl phenylphosphonochloridothioate in 50 milliliters of methylene chloride. After the addition was complete, the mixture was filtered and washed once with 250 milliliters of a 2 percent sodium hydroxide solution and once with 300 milliliters of water. The organic layer was separated and dried over sodium sulfate, filtered and distilled under reduced pressure at 50° C to produce 28 grams (81% of theoretical) of crude 0-(3,5-dichloro-2-pyridinyl) 0-ethyl phenylphosphonothioate as a thick oil. The product was crystallized from a 50:50 mixture of methanol and hexane to produce a white solid which melted at 56°–58° C. The NMR spectra and I.R. spectra confirmed the structure of the product.

Other active ingredients of the present invention are similarly prepared according to the teachings of the specification and the procedures of Example I above by employing the corresponding substituted pyridinol reactant and substituted phosphonochloridothioate. Such other active ingredients include the following:

0-(6-fluoro-2-pyridinyl) 0-ethyl phenylphosphonothioate, an oil having a refractive index of n(25/D) = 1.5721;

0-(5-chloro-2-pyridinyl) 0-ethyl phenylphosphonothioate, an oil having a refractive index of n(25/D) = 1.5898;

0-(5-bromo-3,6-dichloro-2-pyridinyl) 0-methyl phenylphosphonothioate, a crystalline solid having a melting point of 76°–78° C;

0-(6-chloro-2-pyridinyl) 0-ethyl (chlorophenyl)phosphonothioate, an oil having a refractive index of n(25/D) = 1.1593;

0-(4-chloro-2-pyridinyl) 0-methyl phenylphosphonothioate, an oil having a refractive index of n(25/D) = 1.5890;

0-(3,5-dichloro-2-pyridinyl) 0-ethyl (chlorophenyl)phosphonothioate, an oil having a refractive index of n(25/D) = 1.6014;

O-(6-chloro-2-pyridinyl) 0-ethyl (fluorophenyl)phosphonothioate, an oil having a refractive index of n(25/D) = 1.5746;

0-(3,5-dichloro-2-pyridinyl) 0-ethyl (fluorophenyl)phosphonothioate, an oil having a refractive index of n(25/D) = 1.5834;

0-(6-fluoro-2-pyridinyl) 0-ethyl (fluorophenyl)phosphonothioate, an oil having a refractive index of n(25/D) = 1.5514;

0-(5-bromo-2-pyridinyl) 0-methyl phenylphosphonothioate, an oil having a refractive index of n(25/D) = 1.6126;

0-(3,5-dichloro-6-fluoro-2-pyridinyl) 0-methyl phenylphosphonothioate, a solid having a melting point of 81°–83° C;

0-(6-chloro-2-pyridinyl) 0-ethyl phenylphosphonothioate, an oil having a refractive index of n(25/D) = 1.5946;

0-(5-chloro-2-pyridinyl) 0-methyl phenylphosphonothioate, an oil having a refractive index of n(25/D) = 1.5908;

0-(6-bromo-3,5-dichloro-2-pyridinyl) 0-methyl phenylphosphonothioate, a tan waxy solid;

0-(3,6-dichloro-2-pyridinyl) 0-methyl phenylphosphonothioate, an oil having a refractive index of n(25/D) = 1.6057;

0-(3,5-dibromo-2-pyridinyl) 0-methyl phenylphosphonothioate, an oil having a refractive index of n(25/D) = 1.6329;

0-(6-(trifluoromethyl)-2-pyridinyl) 0-methyl phenylphosphonothioate, an oil having a refractive index of n(25/D) = 1.5426;

0-(4,6-dichloro-2-pyridinyl) 0-methyl phenylphosphonothioate, an oil having a refractive index of n(25/D) = 1.5850;

0-(6-bromo-2-pyridinyl) 0-methyl phenylphosphonothioate, an oil having a refractive index of n(25/D) = 1.6169;

0-(3-chloro-2-pyridinyl) 0-propyl phenylphosphonothioate, having a molecular weight of 327.65;

0-(3-bromo-2-pyridinyl) 0-butyl phenylphosphonothioate, having a molecular weight of 386.12;

0-(3-chloro-6-fluoro-2-pyridinyl) 0-butyl phenylphosphonothioate, having a molecular weight of 345.78;

0-(5,6-dichloro-2-pyridinyl) 0-propyl phenylphosphonothioate, having a molecular weight of 362.22;

0-(5-bromo-6-chloro-2-pyridinyl) 0-ethyl phenylphosphonothioate, having a molecular weight of 392.65;

0-(5-bromo-3-chloro-2-pyridinyl) 0-butyl phenylphosphonothioate, having a molecular weight of 420.70;

0-(3,6-dichloro-2-pyridinyl) 0-ethyl phenylphosphonothioate, having a melting point of 44°–46° C.

0-(3-bromo-6-(trifluoromethyl)-2-pyridinyl) 0-methyl phenylphosphonothioate, having a molecular weight of 412.17;

0-(3,5-dichloro-6-(trifluoromethyl)-2-pyridinyl) 0-ethyl phenylphosphonothioate, having a molecular weight of 416.19;

0-(6-chloro-3-(trifluoromethyl)-2-pyridinyl) 0-methyl phenylphosphonothioate, having a molecular weight of 367.72;

0-(3-bromo-6-fluoro-2-pyridinyl) 0-ethyl phenylphosphonothioate, having a molecular weight of 376.20; and 0-(4,6-dichloro-2-pyridinyl) 0-ethyl phenylphosphonothioate, melting at 40° C.

Other substituted pyridine phosphonothioate compounds within the scope of the present invention can also be prepared according to the foregoing teachings and examples.

The active ingredients of the present invention have been found to possess good activity against cotton leafworm larvae (*Spodoptera littoralis* Boisd.). Accordingly, the present invention also comprises methods for controlling cotton leafworm larvae by contacting such organisms and/or their habitats with a pesticidally effective amount of one or more active ingredients. For such uses, unmodified active ingredients of the present invention can be employed. However, the present invention embraces the use of a pesticidally-effective amount of the active ingredients in composition form with an inert material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid pesticidal formulations similarly are well known to the skilled artisan.

As organic solvents used as extending agents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing then in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut sheel flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)-sorbitan monostearate (Tween 60), and sodium dihexyl sulfosuccinate.

The concentration of the active ingredients in liquid compositions generally is from about 0.01 to about 95 percent by weight or more. Concentrations of from about 0.1 to about 50 weight percent are often employed. In dusts or dry formulations, the concentration of the active ingredient can be from about 0.01 to about 95 weight percent or more; concentrations of from about 0.1 to about 50 weight percent are often conveniently employed. In compositions to be employed as concentrates, the active ingredient can be present in a concentration of from about 5 to about 98 weight percent. The active ingredient compositions can also contain other compatible additaments, for example, plant growth regulants, pesticides and the like.

The present compositions can be applied by the use of power-dusters, boom and hand sprayers, spray-dusters and by other conventional means. The compositions can also be applied from airplanes as a dust or a spray.

The exact dosage to be applied is dependent upon the specific active ingredient being employed and it is to be understood that all of the active ingredients of the invention and compositions containing the same may not be equally effective at similar concentrations. The active ingredients of this invention are usually applied at an approximate rate of from about 0.5 to about 4.0 lbs. or more per acre, but lower or higher rates may be appropriate in some cases. A preferred application rate is from 1.0 to about 2.0 pounds per acre. In view of the foregoing and following disclosures, one skilled in the art can readily determine the optimum rate to be applied in any particular case.

So as to illustrate the properties of the active ingredients in the control of cotton leafworm larvae, a group of controlled experiments is described below with representative active ingredients of the present invention.

EXAMPLE IV

A colony of cotton leafworm *Spodoptera littoralis* was reared under laboratory conditions on cotton plant leaves. Second and fourth instar larvae, respectively, were employed for the tests. Aqueous acetone solutions containing various concentrations of 0-(6-chloro-2- pyridinyl) 0-methyl phenylphosponothioate (Compound A) were prepared and cotton plant leaves were dipped in such solutions. Cotton leafworm larvae (10 per treatment) were then allowed to feed on the treated cotton leaves for a period of 24 hours after which the percent (%) mortality was determined as compared to untreated control plants. The treated plants were maintained under conditions conducive to plant and insect growth. The results are set forth in the following Table I.

TABLE I

| Test Compound | Concentration Percent | % Mortality After 24 Hour feeding period | |
|---|---|---|---|
| | | 2nd Instar | 4th Instar |
| Compound A | 0.01 | 80 | 70 |
| | 0.015 | 90 | 70 |
| | 0.02 | 100 | 80 |
| Checks | 0 | 0 | 0 |

The above operations were repeated at various daily intervals following the initial treatment of the plants in order to determine the residual effectiveness of the test ingredient. Additionally, the cotton leafworm larvae were allowed to feed for periods of 48 hours on leaves of the treated plants, the results are set forth in the following Table II.

TABLE II

| Test Cmpd. | Conc. % | % Mortality After 48 Hour Feeding Period at Various Days Following Plant Treatment | | | |
|---|---|---|---|---|---|
| | | 0 | 3 | 5 | 7 |
| Cmpd. A* | 0.012 | 100 | 100 | 100 | 80 |
| | 0.08 | 100 | 100 | 100 | 90 |
| | 0.16 | 100 | 100 | 100 | 100 |
| Cmpd. A** | 0.012 | 100 | 90 | 60 | 60 |
| | 0.08 | 100 | 100 | 80 | 70 |
| | 0.16 | 100 | 100 | 80 | 80 |

*Second Instar larvae.
**Fourth Instar larvae.

EXAMPLE V

Various other active ingredients of the present invention were evaluated according to the procedures of Example IV set forth hereinabove. The cotton leafworm larvae (third instar) were allowed to feed on treated cotton leaves and mortality readings were taken after 24 and 28 hours, respectively. The percent leaf consumed was also evaluated after the 48 hour feeding period. All test ingredients were evaluated at concentrations of 100 parts per million (p.p.m.). The results of such evaluations are set forth in the following Table III:

TABLE III

| Test Compound | % Kill 24 Hrs. | % Kill 48 Hrs. | % Leaf Consumed |
|---|---|---|---|
| 1. 0-(6-fluoro-2-pyridinyl) 0-ethyl phenylphosphonothioate | 90 | 100 | 5 |
| 2. 0-(5-chloro-2-pyridinyl) 0-ethyl phenylphosphonothioate | 90 | 100 | 20 |
| 3. 0-(5-bromo-3,6-dichloro-2-pyridinyl) 0-methyl phenylphosphonothioate | 50 | 100 | 30 |
| 4. 0-(5-bromo-2-pyridinyl) 0-methyl phenylphosphonothioate | 100 | 100 | 15 |
| 5. 0-(3,5-dichloro-6-fluoro-2-pyridinyl) 0-methyl phenylphosphonothioate | 100 | 100 | <5 |
| 6. 0-(3,5-dichloro-2-pyridinyl) 0-methyl phenylphosphonothioate | 0 | 40 | 40 |
| 7. 0-(6-chloro-2-pyridinyl) 0-ethyl phenylphosphonothioate | 100 | — | <5 |
| 8. 0-(6-fluoro-2-pyridinyl) 0-methyl phenylphosphonothioate | 90 | 100 | <5 |
| 9. Control (untreated) | 0 | 0 | 85 |

In comparative operations employing the above procedures and application rate, 0-(3,5,6-trichloro-2-pyridinyl) 0-methyl phenylphosphonothioate (a known compound, see British Pat. No. 1,165,293), was found to give no control after the 24 and 48 hour evaluations and 95 percent of the cotton leaves were found to be consumed. 0-(2-Chloro-3-pyridinyl) 0-methyl phenylphosphonothioate and 0-(2-chloro-4-pyridinyl) 0-methyl phenylphosphonothioate were similarly found to be substantially inactive in the control of cotton leafworm larvae. Such findings clearly support the novelty of the active ingredients herein claimed.

EXAMPLE VI

A spray composition containing 0-(5-chloro-2-pyridinyl) 0-methyl phenylphosphonothioate (Compound B) was prepared as in Example IV and applied to cotton plants in sufficient volume to provide a dosage rate of about 480 grams per acre. Samples of treated cotton leaves were taken at one, three, six, and ten days following treatment and ten 3rd instar larvae of *Spodoptera littoralis* were allowed to feed on the treated leaves. Mortality readings were taken after 24 and 48 hours of feeding and the percent leaf consumed determined after 48 hours. At the 24 hour readings, the compound was found to give 100 percent control of the cotton leafworm larvae after one, three and six days, respectively, with 93 percent control achieved after a period of ten days. 100 Percent control was attained at each of the one, three, six and ten day evaluations after the 48 hour feeding periods. The percent leaf consumed was found to be only 5 percent at the one, three and six day intervals and 8 percent after the ten day period. The untreated check plants were found to be at least 95 percent consumed at each of the evaluation periods.

In other operations, the following compounds were found to give at least 90 percent kill and control of cotton leafworm larvae when applied to the larvae at the dosages indicated below in Table IV.

TABLE IV

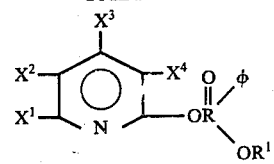

| $X^1$ | $X^2$ | $X^3$ | $X^4$ | $R^1$ | Amount of Test Compound in P.P.M. to Give At Least 90 Percent Kill and Control of Cotton Leafworm Larvae |
|---|---|---|---|---|---|
| —Cl | —H | —Cl | —H | —$C_2H_5$ | 45 |
| —Cl | —H | —Cl | —H | —$CH_3$ | 100 |

-continued

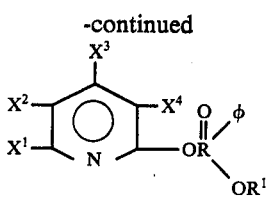

| $X^1$ | $X^2$ | $X^3$ | $X^4$ | $R^1$ | Amount of Test Compound in P.P.M. to Give At Least 90 Percent Kill and Control of Cotton Leafworm Larvae |
|---|---|---|---|---|---|
| —Cl | —Cl | —H | —H | —CH$_3$ | 25 |
| —Cl | —H | —H | —Cl | —CH$_3$ | 60 |
| —Cl | —H | —H | —H | —CH$_3$ | 100 |
| —H | —Cl | —H | —H | —CH$_3$ | 100–200 |
| —H | —H | —H | —Cl | —C$_2$H$_5$ | 400 |
| —H | —H | —Cl | —H | —C$_2$H$_5$ | 400 |
| —H | —Cl | —H | —H | —C$_2$H$_5$ | 100 |
| —Cl | —H | —H | —H | —C$_2$H$_5$ | 100–200 |
| —H | —Cl | —H | —Cl | —C$_2$H$_5$ | 40–50 |
| —Cl | —H | —H | —Cl | —C$_2$H$_5$ | 50 |

The following representative forms for application of the active ingredients of the present invention further illustrate the present invention; where not otherwise expressly stated, "parts" means part by weight. All percentages given therein are calculated on the total weight of the respective composition.

Dust — the following components are employed to produce a 10 percent dust:
10 parts 0-(6-chloro-2-pyridinyl) 0-methyl phenylphosphonothioate;
5 parts of finely dispersed silicic acid having a particle size of about 25 mm and a density of about 2.2 (commercially available under the trademark "Aerosil"), 85 parts talcum.

The active substance is mixed and milled with the carriers. Wettable powders — The following ingredients are used to produce a 10 percent wettable powder:
10 parts 0-(5-chloro-2pyridinyl) 0-methyl phenylphosphonothioate;
3 parts of a mixture of the sodium salts of saturated fatty alcohol sulphates,
5 parts of sodium methylene — bisnaphthalene sulphonate, 82 parts of Kaolin.

The active substances are intimately mixed with the carriers and dispersing agents in suitable mixers and the mixture is milled in corresponding mills and rollers. Wettable powders are obtained which can be diluted with water to form suspensions of any concentration desired.

Emulsion concentrate — To produce a 25 percent emulsion concentrate. 25 Parts of 0-(3,5-dichloro-6-fluoro-2-pyridinyl) 0-methyl phenylphosphonothioate;
2.5 parts of epichlorohydrin;
5 parts of a composition emulsifier consisting of the condensation product of octylphenol and ethylene oxide (average molar ratio of 1:10) and calcium dodecylphenyl sulphonate, in a weight ratio of about 1:1, 67.5 parts of xylene are mixed together. This concentrate can be diluted with water to form emulsions of concentrations suitable for the protection of plants.

The substituted 2-pyridinol and phosphonochloridothioate reactants employed in preparing the active ingredients of the present invention are known and are available or can be prepared according to methods which are known or analogous to those set forth in the known patent or chemical literature.

Although the invention is described with respect to specific modifications, the details thereof are not to be construed as limitations except to the extent indicated in the following claims.

What is claimed is:

1. A compound corresponding to the formula:

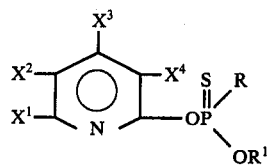

wherein R is phenyl of phenyl being mono- or polysubstituted with bromo, chloro, fluoro or methyl; $R^1$ represents alkyl or 1 to 4 carbon atoms; and $X^1$, $X^2$, $X^3$ and $X^4$ each independently represent bromo, chloro, fluoro, trifluoromethyl or hydrogen, with the proviso that at least one of $X^1$, $X^2$, $X^3$ and $X^4$ is hydrogen; at least one of the others of $X^1$, $X^2$, $X^3$ and $X^4$ is other than hydrogen; with the added proviso that when $X^1$, $X^2$, $X^3$ or $X^4$ is selected from bromo, chloro or fluoro, that no more than two of $X^1$, $X^2$, $X^3$ and $X^4$ can be the same.

2. A compound corresponding to claim 1 wherein R is phenyl and $R^1$ is methyl or ethyl.

3. The compound of claim 2 which is 0-(6-chloro-2-pyridinyl) 0-methyl phenylphosphonothioate.

4. The compound of claim 2 which is 0-(6-fluoro-2-pyridinyl) 0-methyl phenylphosphonothioate.

5. The compound of claim 2 which is 0-(6-fluoro-2-pyridinyl) 0-ethyl phenylphosphonothioate.

6. The compound of claim 2 which is 0-(6-chloro-2-pyridinyl) 0-ethyl phenylphosphonothioate.

7. The compound of claim 2 which is 0-(6-bromo-2-pyridinyl) 0-methyl phenylphosphonothioate.

8. The compound of claim 2 which is 0-(6-trifluoromethyl)-2-pyridinyl) 0-methyl phenylphosphonothioate.

9. The compound according to claim 2 which is 0-(5-bromo-2-pyridinyl) 0-methyl phenylphosphonothioate.

10. The compound according to claim 2 which is 0-(5-chloro-2-pyridinyl) 0-ethyl phenylphosphonothioate.

11. The compound according to claim 2 which is 0-(5-chloro-2-pyridinyl) 0-methyl phenylphosphonothioate.

12. The compound according to claim 2 which is 0-(4-chloro-2-pyridinyl) 0-ethyl phenylphosphonothioate.

13. The compound according to claim 2 which is 0-(3,5-dichloro-2-pyridinyl) 0-methyl phenylphosphonothioate.

14. The compound according to claim 2 which is 0-(3,5-dichloro-2-pyridinyl) 0-ethyl phenylphosphonothioate.

15. The compound according to claim 2 which is 0-(3,5-dibromo-2-pyridinyl) 0-methyl phenylphosphonothioate.

16. The compound according to claim 2 which is 0-(3,6-dichloro-2-pyridinyl) 0-methyl phenylphosphonothioate.

17. The compound according to claim 2 which is 0-(4,6-dichloro-2-pyridinyl) 0-methyl phenylphosphonothioate.

18. The compound according to claim 2 which is 0-(4,6-dichloro-2-pyridinyl) 0-ethyl phenylphosphonothioate.

19. The compound according to claim 2 which is 0-(3,6-dichloro-2-pyridinyl) 0-ethyl phenylphosphonothioate.

20. The compound according to claim 2 which is 0-(5-bromo-3,6-dichloro-2-pyridinyl) 0-methyl phenylphosphonothioate.

21. The compound according to claim 2 which is 0-(3,5-dichloro-6-fluoro-2-pyridinyl) 0-methyl phenylphosphonothioate.

22. The compound according to claim 2 which is 0-(6-bromo-3,5-dichloro-2-pyridinyl) 0-methyl phenylphosphonothioate.

23. A composition comprising a pesticidally-effective amount of a compound of the formula:

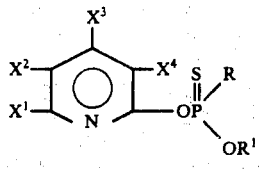

wherein R is phenyl or phenyl being mono- or polysubstituted with bromo, chloro, fluoro or methyl; $R^1$ represents alkyl of 1 to 4 carbon atoms; and $X^1$, $X^2$, $X^3$ and $X^4$ each independently represent bromo, chloro, fluoro, trifluoromethyl or hydrogen, with the proviso that at least one of $X^1$, $X^2$, $X^3$ and $X^4$ is hydrogen; at least one of the others of $X^1$, $X^2$, $X^3$ and $X^4$ is other than hydrogen; with the added proviso that when $X^1$, $X^2$, $X^3$ or $X^4$ is selected from bromo, chloro or fluoro, that no more than two of $X^1$, $X^2$, $X^3$ and $X^4$ can be the same.

24. A composition according to claim 23 wherein R is phenyl and $R^1$ is methyl or ethyl.

25. The composition of claim 24 wherein the compound is 0-(6-chloro-2-pyridinyl) 0-methyl phenylphosphonothioate.

26. The composition of claim 24 wherein the compound is 0-(6-fluoro-2-pyridinyl) 0-methyl phenylphosphonothioate.

27. The composition of claim 24 wherein the compound is 0-(6-fluoro-2-pyridinyl) 0-ethyl phenylphosphonothioate.

28. The composition of claim 24 wherein the compound is 0-(6-chloro-2-pyridinyl) 0-ethyl phenylphosphonothioate.

29. The composition of claim 24 wherein the compound is 0-(6-bromo-2-pyridinyl) 0-methyl phenylphosphonothioate.

30. The composition of claim 24 wherein the compound is 0-(6-trifluoromethyl)-2-pyridinyl) 0-methyl phenylphosphonothioate.

31. The composition of claim 24 wherein the compound is 0-(5-bromo-2-pyridinyl) 0-methyl phenylphosphonothioate.

32. The composition of claim 24 wherein the compound is 0-(5-chloro-2-pyridinyl) 0-ethyl phenylphosphonothioate.

33. The composition of claim 24 wherein the compound is 0-(5-chloro-2-pyridinyl) 0-methyl phenylphosphonothioate.

34. The composition of claim 24 wherein the compound is 0-(4-chloro-2-pyridinyl) 0-methyl phenylphosphonothioate.

35. The composition according to claim 24 wherein the compound is 0-(3,5-dichloro-2-pyridinyl) 0-methyl phenylphosphonothioate.

36. The composition according to claim 24 wherein the compound is 0-(3,5-dichloro-2-pyridinyl) 0-ethyl phenylphosphonothioate.

37. The composition according to claim 24 wherein the compound is 0-(3,5-dibromo-2-pyridinyl) 0-methyl phenylphosphonothioate.

38. The composition according to claim 24 wherein the compound is 0-(3,6-dichloro-2-pyridinyl) 0-methyl phenylphosphonothioate.

39. The composition according to claim 24 wherein the compound is 0-(3,6-dichloro-2-pyridinyl) 0-ethyl phenylphosphonothioate.

40. The composition according to claim 24 wherein the compound is 0-(4,6-dichloro-2-pyridinyl) 0-methyl phenylphosphonothioate.

41. The composition according to claim 24 wherein the compound is 0-(4,6-dichloro-2-pyridinyl) 0-ethyl phenylphosphonothioate.

42. The composition according to claim 24 wherein the compound is 0-(5-bromo-3,6-dichloro-2-pyridinyl) 0-methyl phenylphosphonothioate.

43. The composition according to claim 24 wherein the compound is 0-(3,5-dichloro-6-fluoro-2-pyridinyl) 0-methyl phenylphosphonothioate.

44. The composition according to claim 24 wherein the compound is 0-(6-bromo-3,5-dichloro-2-pyridinyl) 0-methyl phenylphosphonothioate.

45. The composition of claim 24 wherein the inert carrier is a solid.

46. The composition of claim 24 wherein the inert carrier is a liquid.

47. A method for controlling cotton leafworm larvae which comprises contacting said larvae and/or their habitats with a pesticidally-effective amount of composition containing as the active ingredient a compound corresponding to the formula:

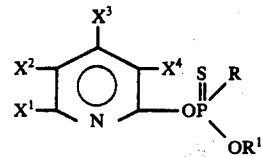

wherein R is phenyl or phenyl being mono- or polysubstituted with bromo, chloro, fluoro or methyl; $R^1$ represents alkyl of 1 to 4 carbon atoms; and $X^1$, $X^2$, $X^3$ and $X^4$ each independently represent bromo, chloro, fluoro, trifluoromethyl or hydrogen, with the proviso that at least one of $X^1$, $X^2$, $X^3$ and $X^4$ is is hydrogen; at least one of the others of $X^1$, $X^2$, $X^3$ and $X^4$ is other than hydrogen; with the added proviso that when $X^1$, $X^2$, $X^3$ or $X^4$ is selected from bromo, chloro or fluoro, that no more than two of $X^1$, $X^2$, $X^3$ and $X^4$ can be the same.

48. The method of claim 47 wherein R is phenyl and $R^1$ is methyl or ethyl.

49. The method of claim 48 wherein the compound is 0-(6-chloro-2-pyridinyl) 0-methyl phenylphosphonothioate.

50. The method of claim 48 wherein the compound is 0-(6-fluoro-2-pyridinyl) 0-methyl phenylphosphonothioate.

51. The method of claim 48 wherein the compound is 0-(6-fluoro-2-pyridinyl) 0-ethyl phenylphosphonothioate.

52. The method of claim 48 wherein the compound is 0-(6-chloro-2-pyridinyl) 0-ethyl phenylphosphonothioate.

53. The method of claim 48 wherein the compound is 0-(6-bromo-2-pyridinyl) 0-methyl phenylphosphonothioate.

54. The method of claim 48 wherein the compound is 0-((6-trifluoromethyl)-2-pyridinyl) 0-methyl phenylphosphonothioate.

55. The method of claim 48 wherein the compound is 0-(5-bromo-2-pyridinyl) 0-methyl phenylphosphonothioate.

56. The method of claim 48 wherein the compound is 0-(5-chloro-2-pyridinyl) 0-ethyl phenylphosphonothioate.

57. The method of claim 48 wherein the compound is 0-(5-chloro-2-pyridinyl) 0-methyl phenylphosphonothioate.

58. The method of claim 48 wherein the compound is 0-(4-chloro-2-pyridinyl) 0-methyl phenylphosphonothioate.

59. The method according to claim 48 wherein the compound is 0-(3,5-dichloro-2-pyridinyl) 0-methyl phenylphosphonothioate.

60. The method according to claim 48 wherein the compound is 0-(3,5-dichloro-2-pyridinyl) 0-ethyl phenylphosphonothioate.

61. The method according to claim 48 wherein the compound is 0-(3,5-dibromo-2-pyridinyl) 0-methyl phenylphosphonothioate.

62. The method according to claim 48 wherein the compound is 0-(3,6-dichloro-2-pyridinyl) 0-methyl phenylphosphonothioate.

63. The method according to claim 48 wherein the compound is 0-(3,6-dichloro-2-pyridinyl) 0-ethyl phenylphosphonothioate.

64. The method according to claim 48 wherein the compound is 0-(4,6-dichloro-2-pyridinyl) 0-methyl phenylphosphonothioate.

65. The method according to claim 48 wherein the compound is 0-(4,6-dichloro-2-pyridinyl) 0-ethyl phenylphosphonothioate.

66. The method according to claim 48 wherein the compound is 0-(5-bromo-3,6-dichloro-2-pyridinyl) 0-methyl phenylphosphonothioate.

67. The method according to claim 48 wherein the compound is 0-(3,5-dichloro-6-fluoro-2-pyridinyl) 0-methyl phenylphosphonothioate.

68. The method according to claim 48 wherein the compound is 0-(6-bromo-3,5-dichloro-2-pyridinyl) 0-methyl phenylphosphonothioate.

* * * * *

UNITED STATES PATENT AND TRADEMARK OFFICE
CERTIFICATE OF CORRECTION

PATENT NO. : 4,115,557
DATED : September 19, 1978
INVENTOR(S) : Chester E. Pawloski It is certified that error appears in the above-identified patent and that said Letters Patent are hereby corrected as shown below:

Column 4, line 30, "grams" should read -- gram --;

Column 7, line 59, "sheel" should read -- shell --;

Column 9, line 1, "phenylphosponothioate" should read -- phenylphosphonothioate --;

Column 9, line 47 "28" should read -- 48 --;

Column 11, line 24 "part by weight" should read -- parts by weight --;

Column 11, line 38 "2pyridinyl" should read -- 2-pyridinyl --;

Column 11, line 54 "composition" should read -- composite --;

Column 12, line 36 "0-(6" should read -- 0-((6 --;

Column 13, line 52 "0-(6" should read -- 0-((6 --.

Signed and Sealed this

Ninth Day of January 1979

[SEAL]

Attest:

RUTH C. MASON
Attesting Officer

DONALD W. BANNER
Commissioner of Patents and Trademarks